US011793469B2

(12) United States Patent
Kim et al.

(10) Patent No.: US 11,793,469 B2
(45) Date of Patent: Oct. 24, 2023

(54) IDENTIFYING RELIABLE VECTORS

(71) Applicant: West Affum Holdings Corp., Grand Cayman (KY)

(72) Inventors: Jaeho Kim, Redmond, WA (US); Joseph L. Sullivan, Kirkland, WA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 191 days.

(21) Appl. No.: 17/355,105

(22) Filed: Jun. 22, 2021

(65) Prior Publication Data
US 2022/0151566 A1    May 19, 2022

Related U.S. Application Data

(60) Provisional application No. 63/114,956, filed on Nov. 17, 2020.

(51) Int. Cl.
| | |
|---|---|
| *A61N 1/39* | (2006.01) |
| *A61B 5/00* | (2006.01) |
| *A61B 5/0245* | (2006.01) |
| *A61B 5/30* | (2021.01) |
| *A61B 5/364* | (2021.01) |
| *A61B 5/347* | (2021.01) |

(52) U.S. Cl.
CPC .......... *A61B 5/7221* (2013.01); *A61B 5/0245* (2013.01); *A61B 5/30* (2021.01); *A61B 5/347* (2021.01); *A61B 5/364* (2021.01); *A61N 1/3904* (2017.08)

(58) Field of Classification Search
CPC ....... A61B 5/7221; A61B 5/352; A61B 5/364; A61N 1/3904
See application file for complete search history.

(56) References Cited

U.S. PATENT DOCUMENTS

| | | |
|---|---|---|
| 3,724,455 A | 4/1973 | Unger |
| 4,583,524 A | 4/1986 | Hutchins |
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |

(Continued)

OTHER PUBLICATIONS

The LifeVest Network/Patient Data Management System, Zoll, 2015, 2000503 Rev A.

(Continued)

*Primary Examiner* — George R Evanisko
(74) *Attorney, Agent, or Firm* — Columbia IP Law

(57) ABSTRACT

In one embodiment, a method to determine reliable electrocardiogram (ECG) signal is described. The method includes receiving at least one ECG signal for a period of time from a patient. The method also includes analyzing the at least one ECG signal to determine a first heart rate using a first method and analyzing the at least one ECG signal to determine a second heart rate using a second method different from the first method. The method includes comparing the first and second heart rates to each other and classifying the at least one ECG signal as reliable when a reliability threshold is satisfied.

20 Claims, 9 Drawing Sheets

(56) References Cited

U.S. PATENT DOCUMENTS

| | | |
|---|---|---|
| RE34,800 E | 11/1994 | Hutchins |
| 5,394,892 A | 3/1995 | Kenny |
| 5,405,362 A | 4/1995 | Kramer et al. |
| 5,474,574 A | 12/1995 | Payne et al. |
| 5,662,690 A | 9/1997 | Cole et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 7/2002 | Owen et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 10/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,592,403 B2 | 3/2017 | Sullivan |
| 11,096,628 B2 * | 8/2021 | Wang .............. A61B 5/024 |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0025131 A1 | 1/2014 | Sullivan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0328472 A1 | 11/2015 | Sullivan et al. |
| 2016/0004831 A1 | 1/2016 | Carlson et al. |
| 2016/0082277 A1 | 3/2016 | Foshee, Jr. et al. |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

* cited by examiner

IDENTIFYING RELIABLE VECTORS

CROSS-REFERENCE TO RELATED PATENT APPLICATIONS

This patent application claims benefit of U.S. Provisional Patent Application No. 63/114,956 filed Nov. 11, 2020, and is incorporated herein by reference in their entirety for all purposes.

BACKGROUND

When people suffer from some types of heart arrhythmias, in some instances, blood flow to various parts of the body may be reduced. Some arrhythmias can result in a Sudden Cardiac Arrest (SCA). SCA can lead to death very quickly, e.g., within 10 minutes, unless treated in the interim. Some observers have thought that SCA is the same as a heart attack, which it is not.

Some people have an increased risk of SCA. Such people may include patients who have had a heart attack or a prior SCA episode. A frequent recommendation for these people is to receive an Implantable Cardioverter Defibrillator (ICD). The ICD is surgically implanted in the chest and continuously monitors the patient's intracardiac electrogram (IEGM). If certain types of heart arrhythmias are detected, then the ICD delivers an electric shock through the heart.

As a further precaution, people who have been identified to have an increased risk of SCA are sometimes given a Wearable Cardioverter Defibrillator (WCD) system to wear until an ICD is implanted. Early versions of such systems were called wearable cardiac defibrillator systems. A WCD system typically includes a harness, vest, belt, or another garment that the patient wears. The WCD system further includes electronic components, such as a defibrillator and electrodes, coupled to the harness, vest, or another garment. When the patient wears the WCD system, the electrodes may electrically contact the patient's skin and aid in sensing the patient's electrocardiogram (ECG). If a shockable heart arrhythmia (e.g., ventricular fibrillation or VF) is detected from the ECG, then the defibrillator delivers an appropriate electric shock through the patient's body through the heart. The delivered shock may restart the patient's heart and save the patient's life.

BRIEF SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present disclosure describes instances and examples of cardiac monitoring systems (e.g., WCD systems), devices, systems, storage media that may store programs and methods.

In one embodiment, a method to determine reliable electrocardiogram (ECG) signal is described. The method includes receiving at least one ECG signal for a period of time from a patient. The method also includes analyzing the at least one ECG signal to determine a first heart rate using a first method and analyzing the at least one ECG signal to determine a second heart rate using a second method different from the first method. The method includes comparing the first and second heart rates to each other and classifying the at least one ECG signal as reliable when a reliability threshold is satisfied.

In some embodiments, the method includes performing a rhythm analysis using at least the first heart rate when the ECG signal is classified as reliable. In some embodiments, the first method may be a time domain method and the second method may be a frequency domain method. In some embodiments, the at least one ECG signal may be classified as reliable when the first and second heart rates are within a predetermined number of beats. In some embodiments, the predetermined number of beats may be within 5-15 beats per minute. In some embodiments, the predetermined number of beats may be within 10 beats per minute.

In some embodiments, the at least one ECG signal may be classified as reliable when the first and second heart rates are within a predetermined percentage difference. In some embodiments, the predetermined percentage difference may be equal to or between 1 percent and 15 percent. In further embodiments, the predetermined percentage difference may be within 10 percent.

In some embodiments, the method may include classifying the at least one ECG signal as unreliable when an unreliability threshold is satisfied. In some embodiments, the unreliability threshold may be equal to or greater than 10 percent. In some embodiments, the first method or second method may include one of an adaptive signal processing, Kalman filtering, independent component analysis, and principal component analysis.

In some embodiments, the at least one ECG signal may include three or more signals. In some embodiments, at least two ECG signals may be classified as reliable. In some embodiments, the method may include performing a rhythm analysis using a mathematical combination of heart rates from the at least two ECG signals. In some instances, the mathematical combination may be a weighted average of all reliable ECG signals.

In some embodiments, the method may include receiving physiological data from the patient for the period of time and analyzing the physiological data for a shockable condition. In some embodiments, the physiological data may include blood volume data. In some instances, the blood volume data is used to confirm a shockable condition.

In another embodiment, a wearable cardioverter defibrillator (WCD) is described. The WCD includes a support structure wearable by a person, a processor coupled to the support structure, at least three sensing electrodes in communication with the processor, and a discharge circuit configured to discharge a stored electrical charge through a body of the patient. The discharge circuit is in communication with the processor. The processor is configured to receive at least one ECG signal for a period of time from the person, analyze the at least one ECG signal to determine a first heart rate using a first method, analyze the at least one ECG signal to determine a second heart rate using a second method different from the first method, compare the first and second heart rates to each other, and classify the at least one ECG signal as reliable when a reliability threshold is satisfied In some embodiments, the processor may be configured to perform a rhythm analysis using at least the first heart rate when the ECG signal is classified as reliable. In some embodiments, the first method may be a time domain method and the second method may be a frequency domain method. In some embodiments, the at least one ECG signal may be classified as reliable when the first and second heart rates are within a predetermined number of beats. In some embodiments, the predetermined number of beats may be within 5-15 beats per minute. In some embodiments, the predetermined number of beats may be within 10 beats per minute.

In some embodiments, the at least one ECG signal may be classified as reliable when the first and second heart rates are within a predetermined percentage difference. In some embodiments, the predetermined percentage difference may be equal to or between 1 percent and 15 percent. In further embodiments, the predetermined percentage difference may be 10 percent.

In some embodiments, the processor may be configured to classify the at least one ECG signal as unreliable when an unreliability threshold is satisfied. In some embodiments, the unreliability threshold may be equal to or greater than 10 percent. In some embodiments, the first method or second method may include one of an adaptive signal processing, Kalman filtering, independent component analysis, and principal component analysis.

In some embodiments, the at least one ECG signal may include three or more signals. In some embodiments, at least two ECG signals may be classified as reliable. In some embodiments, the processor may be configured to perform a rhythm analysis using a mathematical combination of heart rates from the at least two ECG signals. In some instances, the mathematical combination may be a weighted average of all reliable ECG signals.

In some embodiments, the processor may be configured to receive physiological data from the patient for the period of time and analyzing the physiological data for a shockable condition. In some embodiments, the physiological data may include blood volume data. In some instances, the blood volume data is used to confirm a shockable condition.

In another embodiment, a method to monitor a heart of a patient is described. The method includes receiving at least one ECG signal for a period of time from a patient. The method also includes analyzing the at least one ECG signal to determine a first heart rate using a first method and analyzing the at least one ECG signal to determine a second heart rate using a second method different from the first method. The first method is a time domain method and the second method is a frequency domain method. The method also includes comparing the first and second heart rates to each other and classifying the at least one ECG signal as reliable when a reliability threshold is satisfied. The method then performs a rhythm analysis using at least the first heart rate when the ECG signal is classified as reliable.

BRIEF DESCRIPTION OF THE DRAWINGS

The foregoing aspects and many of the attendant advantages of this disclosure will become more readily appreciated as the same becomes better understood by reference to the following detailed description, when taken in conjunction with the accompanying drawings, wherein.

DETAILED DESCRIPTION

The detailed description set forth below in connection with the appended drawings, where like numerals reference like elements, are intended as a description of various embodiments of the present disclosure and are not intended to represent the only embodiments. Each embodiment described in this disclosure is provided merely as an example or illustration and should not be construed as precluding other embodiments. The illustrative examples provided herein are not intended to be exhaustive or to limit the disclosure to the precise forms disclosed.

In the following description, specific details are set forth to provide a thorough understanding of exemplary embodiments of the present disclosure. It will be apparent to one skilled in the art, however, that the embodiments disclosed herein may be practiced without embodying all of the specific details. In some instances, well-known process steps have not been described in detail in order not to unnecessarily obscure various aspects of the present disclosure. Further, it will be appreciated that embodiments of the present disclosure may employ any combination of features described herein.

Wearable Cardioverter Defibrillators (WCDs) are worn by patients at risk for sudden cardiac arrest and other potential heart conditions. Because WCDs are worn by ambulatory patients, noise on an ECG signal may be generated at the electrode-skin interface. For example, patient movement may cause movement at the electrode-skin interface to generate noise that may interfere with ECG interpretation. This noise may then interfere with obtaining accurate heart-rate signals, which may result in a missed cardiac episode.

In some embodiments, a WCD device may have four monitoring electrodes that can generate six differential ECG vectors. During patient movement, some ECG vectors may be noisier than other ECG vectors. As described herein, identifying more reliable ECG vectors for ECG characteristic assessment provides greater reliability. Some of the ECG vectors may produce a relatively cleaner ECG signal and some may produce a noisier signal. To make the best ECG characteristics assessment, a WCD needs to assess which of the ECG vectors are reliable for the assessment.

For exemplary purposes only, the embodiments herein will be described in reference to a WCD system and a defibrillator. However, the methodology for determining a reliable ECG vector can be performed by a WCD or any wearable medical monitoring device that monitors a patient's ECG.

Figure 1:
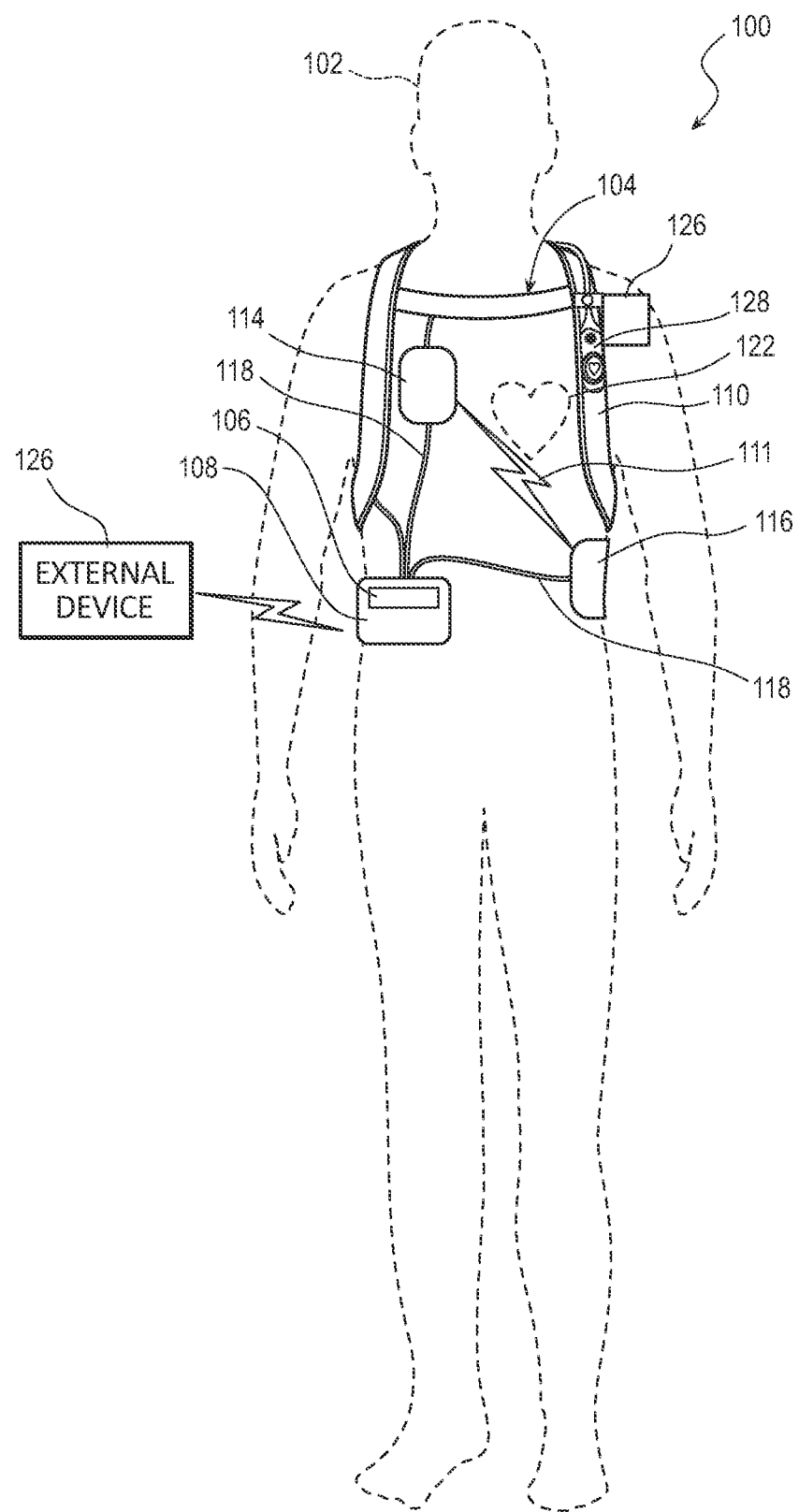
FIG. 1 is a diagram of a sample WCD system in accordance with exemplary embodiments described herein.

FIG. 1 illustrates a system 100 with a patient 102 wearing an example of a WCD system 104 according to embodiments described herein. In some embodiments, the WCD system 104 may include one or more communication devices 106, a support structure 110, and an external defibrillator 108 connected to two or more defibrillation electrodes 114, 116, among other components.

The support structure 110 may be worn by the patient 102. The patient 102 may be ambulatory, meaning the patient 102 can walk around and is not necessarily bed-ridden while wearing the wearable portion of the WCD system 104. While the patient 102 may be considered a "user" of the WCD system 104, this is not a requirement. For instance, a user of the WCD system 104 may also be a clinician such as a doctor, nurse, emergency medical technician (EMT), or other similarly tasked individual or group of individuals. In some cases, a user may even be a bystander. The particular context of these and other related terms within this description should be interpreted accordingly.

In some embodiments, the support structure 110 may include a vest, shirt, series of straps, or other system enabling the patient 102 to carry at least a portion of the WCD system 104 on the patient's body. In some embodiments, the support structure 110 may comprise a single component. For example, the support structure 110 may comprise a vest or shirt that properly locates the WCD system 104 on a torso 112 of the patient 102. The single component of the support structure 110 may additionally carry or couple to all of the various components of the WCD system 104.

In other embodiments, the support structure 110 may comprise multiple components. For example, the support structure 110 may include a first component resting on a patient's shoulders. The first component may properly locate a series of defibrillation electrodes 114, 116 on the torso 112 of the patient 102. A second component may rest more towards a patient's hips, whereby the second component may be positioned such that the patient's hips support the heavier components of the WCD system 104. In some embodiments, the heavier components of the WCD system 104 may be carried via a shoulder strap or may be kept close to the patient 102, such as in a cart, bag, stroller, wheelchair, or another vehicle.

The external defibrillator 108 may be coupled to the support structure 110 or may be carried remotely from the patient 102. The external defibrillator 108 may be triggered to deliver an electric shock to the patient 102 when patient 102 wears the WCD system 104. For example, if certain thresholds are exceeded or met, the external defibrillator 108 may engage and deliver a shock to the patient 102.

The defibrillation electrodes 114, 116 can be configured to be worn by patient 102 in a number of ways. For instance, the defibrillator 108 and the defibrillation electrodes 114, 116 can be coupled to the support structure 110 directly or indirectly. For example, the support structure 110 can be configured to be worn by the patient 102 to maintain at least one of the electrodes 114, 116 on the body of the patient 102, while the patient 102 is moving around, etc. The electrodes 114, 116 can be thus maintained on the torso 112 by being attached to the skin of patient 102, simply pressed against the skin directly or through garments, etc. In some embodiments, the electrodes 114, 116 are not necessarily pressed against the skin but become biased that way upon sensing a condition that could merit intervention by the WCD system 104. In addition, many of the components of defibrillator 108 can be considered coupled to support structure 110 directly or indirectly via at least one of the defibrillation electrodes 114, 116.

The WCD system 104 may defibrillate the patient 102 by delivering an electrical charge, pulse, or shock 111 to the patient 102 through a series of electrodes 114, 116 positioned on the torso 112. For example, when defibrillation electrodes 114, 116 are in good electrical contact with the torso 112 of patient 102, the defibrillator 108 can administer, via electrodes 114, 116, a brief, strong electric pulse 111 through the body. The pulse 111 is also known as shock, defibrillation shock, therapy, electrotherapy, therapy shock, etc. The pulse 111 is intended to go through and restart heart 122 in an effort to save the life of patient 102. The pulse 111 can further include one or more pacing pulses of lesser magnitude to pace heart 122 if needed. The electrodes 114, 116 may be electrically coupled to the external defibrillator 108 via a series of electrode leads 118. The defibrillator 108 may administer an electric shock 111 to the body of the patient 102 when the defibrillation electrodes 114, 116 are in good electrical contact with the torso 112 of patient 102. In some embodiments, devices (not shown) proximate the electrodes 114, 116 may emit a conductive fluid to encourage electrical contact between the patient 102 and the electrodes 114, 116.

In some embodiments, the WCD system 104 may also include either an external or internal monitoring device or some combination thereof. FIG. 1 displays an external monitoring device 124, which may also be known as an outside monitoring device. The monitoring device 124 may monitor at least one local parameter. Local parameters may include a physical state of the patient 102, such as ECG, movement, heart rate, pulse, temperature, and the like. Local parameters may also include a parameter of the WCD 104, environmental parameters, or the like. The monitoring device 124 may be physically coupled to the support structure 110 or may be proximate to the support structure 110. In either location, the monitoring device 124 is communicatively coupled with other components of the WCD 104.

For some of these parameters, the device 124 may include one or more sensors or transducers. Each one of such sensors can be configured to sense a parameter of the patient 102 and to render an input responsive to the sensed parameter. In some embodiments, the input is quantitative, such as values of a sensed parameter; in other embodiments, the input is qualitative, such as informing whether or not a threshold is crossed. In some instances, these inputs about the patient 102 are also referred to herein as patient physiological inputs and patient inputs. In some embodiments, a sensor can be construed more broadly as encompassing many individual sensors. In some instances, the device 124 may include a blood volume sensor. According to embodiments of the present disclosure, the blood volume sensor may include communication circuitry to communicate with the WCD system so that HR and blood volume measurements can be provided to the WCD system.

In some embodiments, a communication device 106 may enable the patient 102 to interact with and garnish data from the WCD system 104. The communication device 106 may enable a patient or third party to view patient data, dismiss a shock if the patient is still conscious, turn off an alarm, and otherwise engage with the WCD system 104. In some embodiments, the communication device 106 may be a separable part of an external defibrillator 108. For example, the communication device 106 may be a separate device coupled to the external defibrillator 108. In some embodiments, the communication device 106 may be wired or wirelessly linked to the external defibrillator 108 and may be removable from the defibrillator 108. In other embodiments, the communication device 106 may form an inseparable assembly and share internal components with the external defibrillator 108. In some embodiments, the WCD system 104 may include more than one communication device 106. For example, the defibrillator 108 may include components able to communicate to the patient, and the WCD system 104 may include a separate communication device 106 remote from the defibrillator 108.

In some embodiments, the communication device 106 may be communicatively coupled to an alert button 128. The alert button 128 may be removably coupled to the support structure 110. The patient 102 may couple the alert button 128 to the support structure 110 or may couple the alert button 128 to an article of clothing. The alert button 128 may have a wired or wireless connection to the communication device 106. In some embodiments, the alert button 128 may include a visual output, an audio output, and a user input. The visual output may include a light, such as an LED, a small screen, or some combination thereof. Likewise, the audio output may include one or more speakers. The output of the audio output may be loud enough to be heard over nominal background noise. In some embodiments, the audio output might have an adjustable volume range. In some embodiments, the alert button 128 may include a microphone. In still further embodiments, the alert button 128 may also include a haptic response.

In some embodiments, the defibrillator 108 may connect with one or more external devices 126. For example, as shown in FIG. 1, the defibrillator 108 may connect to various external devices 126 such as the cloud, a remote desktop, a laptop, a mobile device, or other external device using a network such as the Internet, local area networks, wide area networks, virtual private networks (VPN), other communication networks or channels, or any combination thereof.

In embodiments, one or more of the components of the exemplary WCD system 104 may be customized for the patient 102. Customization may include a number of aspects including, but not limited to, fitting the support structure 110 to the torso 112 of patient 102; baseline physiological parameters of patient 102 can be measured, such as the heart rate of patient 102 while resting, while walking, motion detector outputs while walking, etc. The measured values of such baseline physiological parameters can be used to customize the WCD system in order to make its diagnoses more accurate since patients' bodies differ from one another. Of course, such parameter values can be stored in a memory of the WCD system and the like. Moreover, a programming interface can be made according to embodiments, which receives such measured values of baseline physiological parameters. Such a programming interface may input automatically in the WCD system these, along with other data.

Figure 2:
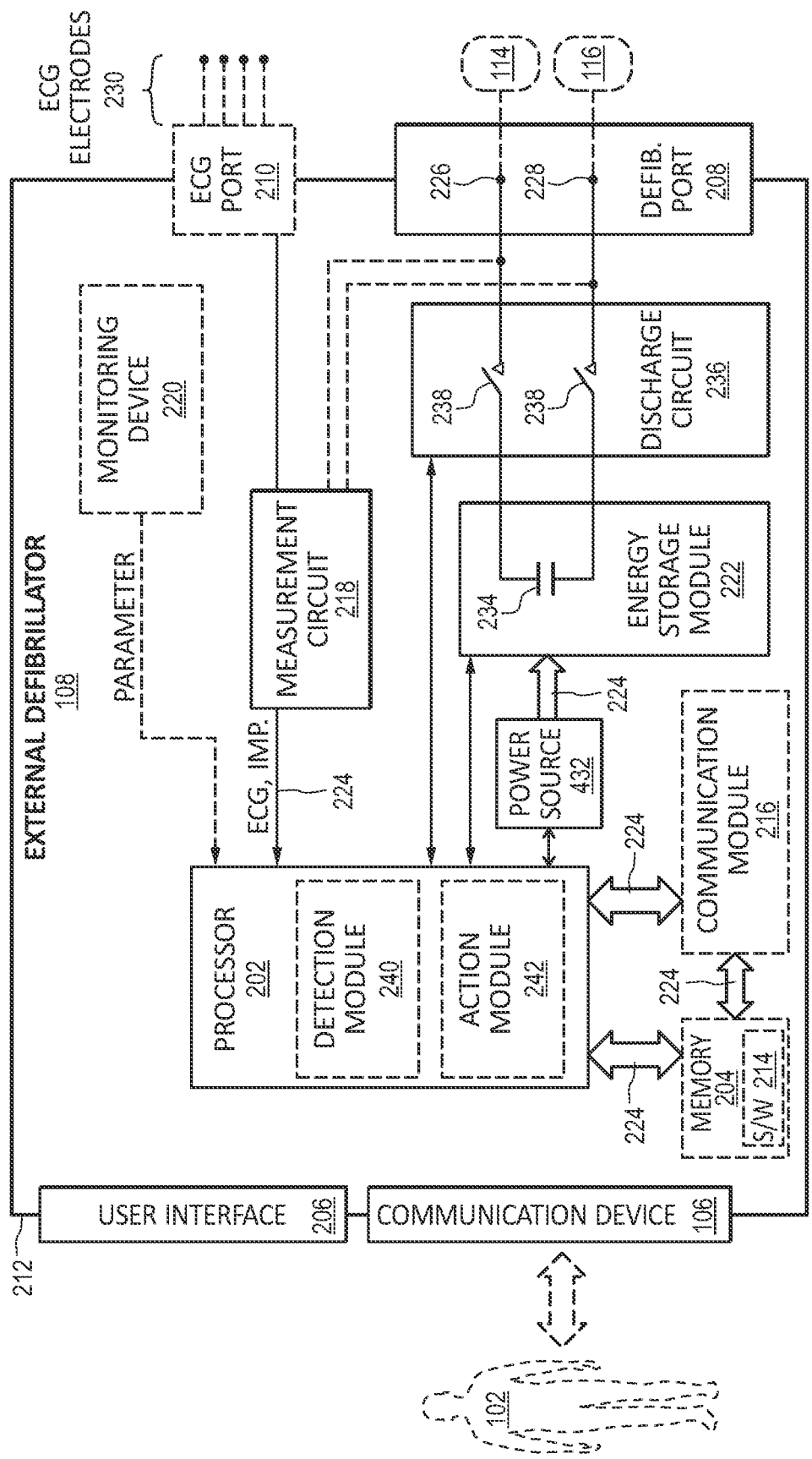
FIG. 2 is a block diagram of an example defibrillator in accordance with exemplary embodiments described herein.

FIG. 2 is a diagram displaying various components of an example external defibrillator 108. The external defibrillator 108 may be an example of the defibrillator 108 described with reference to FIG. 1. The components shown in FIG. 2 may be contained within a single unit or may be separated amongst two or more units in communication with each other. The defibrillator 108 may include a communication device 106, processor 202, memory 204, defibrillation port 208, and ECG port 210, among other components. In some embodiments, the components are contained within a housing 212 or casing. The housing 212 may comprise a hard shell around the components or may comprise a softer shell for increased patient comfort.

The communication device 106, processor 202, memory 204 (including software/firmware code (SW) 214), defibrillation port 208, ECG port 210, communication module 216, measurement circuit 218, monitoring device 220, and energy storage module 222 may communicate, directly or indirectly, with one another via one or more buses 224. The one or more buses 224 may allow data communication between the elements and/or modules of the defibrillator 108.

The memory 204 may include random access memory (RAM), read-only memory (ROM), flash RAM, and/or other types. The memory 204 may store computer-readable, computer-executable software/firmware code 214, including instructions that, when executed, cause the processor 202 to perform various functions (e.g., determine shock criteria, determine consciousness of patient, track patient parameters, establish electrode channels, determine noise levels in electrode readings, etc.). In some embodiments, the processor 202 may include an intelligent hardware device, e.g., a central processing unit (CPU), a microcontroller, an application-specific integrated circuit (ASIC), etc.

In some embodiments, the memory 204 can contain, among other things, the Basic Input-Output system (BIOS), which may control basic hardware and/or software operations such as interactions and workings of the various components of the defibrillator 108, and in some embodiments, components external to the defibrillator 108. For example, the memory 204 may contain various modules to implement the workings of the defibrillator 108 and other aspects of the present disclosure.

In some embodiments, the defibrillator 108 may include a user interface 206. The user interface 206 may be in addition to or part of the communication device 106. The user interface 206 may display an ECG of the patient, a status of the defibrillator 108, a status of a charge (e.g., a battery charge or an energy storage module), and the like.

In some embodiments, the defibrillator 108 may include a defibrillation port 208. The defibrillation port 208 may comprise a socket, opening, or electrical connection in the housing 212. In some instances, the defibrillation port 208 may include two or more nodes 226, 228. The two or more nodes 226, 228 may accept two or more defibrillation electrodes (e.g., defibrillation electrodes 114, 116, FIG. 1). The nodes 226, 228 may provide an electrical connection between the defibrillation electrodes 114, 116 and the defibrillator 108. The defibrillation electrodes 114, 116 may plug into the two or more nodes 226, 228 via one or more leads (e.g., leads 118), or, in some instances, the defibrillation electrodes 114, 116 may be hardwired to the nodes 226, 228. Once an electrical connection is established between the defibrillation port 208 and the electrodes 114, 116, the defibrillator 108 may be able to deliver an electric shock to the patient 102.

In some embodiments, the defibrillator 108 may include an ECG port 210 in the housing 212. The ECG port 210 may accept one or more ECG electrodes 230 or ECG leads. In some instances, the ECG electrodes 230 sense a patient's ECG signal. For example, the ECG electrodes 230 may record electrical activity generated by heart muscle depolarization. The ECG electrodes 230 may utilize 4-leads to 12-leads or multichannel ECG, or the like. The ECG electrodes 230 may connect with the patient's skin.

In some embodiments, the defibrillator 108 may include a measurement circuit 218. The measurement circuit 218 may be in communication with the ECG port 210. For example, the measurement circuit 218 may receive physiological signals from ECG port 210. The measurement circuit 218 may additionally or alternatively receive physiological signals via the defibrillation port 208 when defibrillation electrodes 114, 116 are attached to the patient 102. The measurement circuit 218 may determine a patient's ECG signal from a difference in voltage between the defibrillation electrodes 114, 116.

In some embodiments, the measurement circuit 218 may monitor the electrical connection between the defibrillation electrodes 114, 116 and the skin of the patient 102. For example, the measurement circuit 218 can detect impedance between electrodes 114, 116. The impedance may indicate the effective resistance of an electric circuit. An impedance calculation may determine when the electrodes 114, 116 have a good electrical connection with the patient's body.

In some embodiments, the defibrillator 108 may include an internal monitoring device 220 within the housing 212. The monitoring device 220 may monitor at least one local parameter. Local parameters may include the physical state of the patient, such as ECG, movement, heart rate, pulse, temperature, and the like. Local parameters may also include a parameter of the WCD system (e.g., WCD 104, FIG. 1), defibrillator 108, environmental parameters, or the like.

In some embodiments, the WCD system 104 may include an internal monitoring device 220 and an external monitoring device (e.g., external monitoring device 124). If both monitoring devices 124, 220 are present, the monitoring devices 124, 220 may work together to parse out specific parameters depending on position, location, and other factors. For example, the external monitoring device 124 may monitor environmental parameters while the internal monitoring device 220 may monitor patient and system parameters.

Patient parameters may include patient physiological parameters. Patient physiological parameters may include, for example and without limitation, those physiological parameters that can be of any help in detecting by the WCD system whether or not the patient is in need of a shock or other intervention or assistance. Patient physiological parameters may also optionally include the patient's medical history, event history and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 124, 220 may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an SpO2 sensor, and so on. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection.

In some embodiments, the local parameter is a trend that can be detected in a monitored physiological parameter of patient. A trend can be detected by comparing values of parameters at different times over short and long terms. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2, CO2, or other parameters such as those mentioned above, f) respiratory function, respiratory rate, etc.; g) motion, level of activity; and so on. Once a trend is detected, it can be stored and/or reported via a communication link, along perhaps with a warning if warranted. From the report, a physician monitoring the progress of patient will know about a condition that is either not improving or deteriorating.

Patient state parameters include recorded aspects of patient, such as motion, posture, whether they have spoken recently plus maybe also what they said, and so on, plus optionally the history of these parameters. In another embodiment, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may thus include a motion detector. In embodiments, a motion detector can be implemented within monitoring device 124 or monitoring device 220. Such a motion detector can be made in many ways as is known in the art, for example by using an accelerometer. In this example, a motion detector is implemented within one of the monitoring devices 124, 220. A motion detector of a WCD system according to embodiments can be configured to detect a motion event. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed, if monitoring device 124, 220 includes a GPS location sensor as per the above, and if it is presumed that the patient is wearing the WCD system.

In some embodiments, the defibrillator 108 may include a power source 232. The power source 232 may comprise a battery or battery pack, which may be rechargeable. In some instances, the power source 232 may comprise a series of different batteries to ensure the defibrillator 108 has power. For example, the power source 232 may include a series of rechargeable batteries as a prime power source and a series of non-rechargeable batteries as a secondary source. If the patient 102 is proximate to an AC power source, such as when sitting down, sleeping, or the like, the power source 232 may include an AC override wherein the power source 232 draws power from the AC source.

In some embodiments, the defibrillator 108 may include an energy storage module 222. The energy storage module 222 may store electrical energy in preparation or anticipation of providing a sudden discharge of electrical energy to the patient. In some embodiments, the energy storage module 222 may have its own power source and/or battery pack. In other embodiments, the energy storage module 222 may pull power from the power source 232. In still further embodiments, the energy storage module 222 may include one or more capacitors 234. The one or more capacitors 234 may store an electrical charge, which may be administered to the patient. The processor 202 may be communicatively coupled to the energy storage module 222 to trigger the amount and timing of electrical energy to provide to the defibrillation port 208 and, subsequently, the patient 102.

In some embodiments, the defibrillator 108 may include a discharge circuit 236. The discharge circuit 236 may control the energy stored in the energy storage module 222. For example, the discharge circuit 236 may either electrically couple or decouple the energy storage module 222 to the defibrillation port 208. The discharge circuit 236 may be communicatively coupled to the processor 202 to control when the energy storage module 222 and the defibrillation port 208 should or should not be coupled to either administer or prevent a charge from emitting from the defibrillator 108. In some embodiments, the discharge circuit 236 may include one or more switches 238. In further embodiments, the one or more switches 238 may include an H-bridge.

In some embodiments, the defibrillator 108 may include a communication module 216. The communication module 216 may establish one or more communication links with either local hardware and/or software to the WCD system 104 and defibrillator 108 or to remote hardwire separate from the WCD system 104. In some embodiments, the communication module 216 may include one or more antennas, processors, and the like. The communication module 216 may communicate wirelessly via radio frequency, electromagnetics, local area networks (LAN), wide area networks (WAN), virtual private networks (VPN), RFID, Bluetooth, cellular networks, and the like. The communication module 216 may facilitate communication of data and commands such as patient data, episode information, therapy attempted, CPR performance, system data, environmental data, and so on.

In some embodiments, the communication module 216 may establish one or more wired or wireless communication links with other devices of other entities, such as a remote assistance center, Emergency Medical Services (EMS), and so on. The communication links can be used to transfer data and commands. The data may be patient data, event information, therapy attempted, CPR performance, system data, environmental data, and so on. For example, communication module 216 may transmit wirelessly, e.g. on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. In some embodiments, the communication module 216 may also include such interconnected sub-components as may be deemed necessary by a person skilled in the art, for example an antenna, portions of a processor, supporting electronics, outlet for a telephone or a network cable, etc.

In some embodiments, the processor 202 may execute one or more modules. For example, the processor 202 may execute a detection module 240 and/or an action module 242. The detection module 240 may be a logic device or algorithm to determine if any or a variety of thresholds are exceeded, which may require an action from the defibrillator 108. For example, the detection module 240 may receive and interpret all of the signals from the ECG port 210, the defibrillation port 208, the monitoring device 220, an external monitoring device, and the like. The detection module 240 may process the information to ensure the patient is still conscious and healthy. If any parameter indicates the patient 102 may be experiencing distress or indicating a cardiac episode, the detection module 240 may activate the action module 242.

The action module 242 may receive data from the detection module 240 and perform a series of actions. For example, an episode may merely be a loss of battery power at the power source 232 or the energy storage module 222, or one or more electrodes (e.g., ECG electrodes, defibrillation electrodes) may have lost connection. In such instances, the action module 242 may trigger an alert to the patient or to an outside source of the present situation. This may include activating an alert module. If an episode is a health risk, such as a cardiac event, the action module 242 may begin a series of steps. This may include issuing a warning to the patient, issuing a warning to a third party, priming the energy storage module 222 for defibrillation, releasing one or more conductive fluids proximate defibrillation electrodes 114, 116, and the like.

Figure 3:
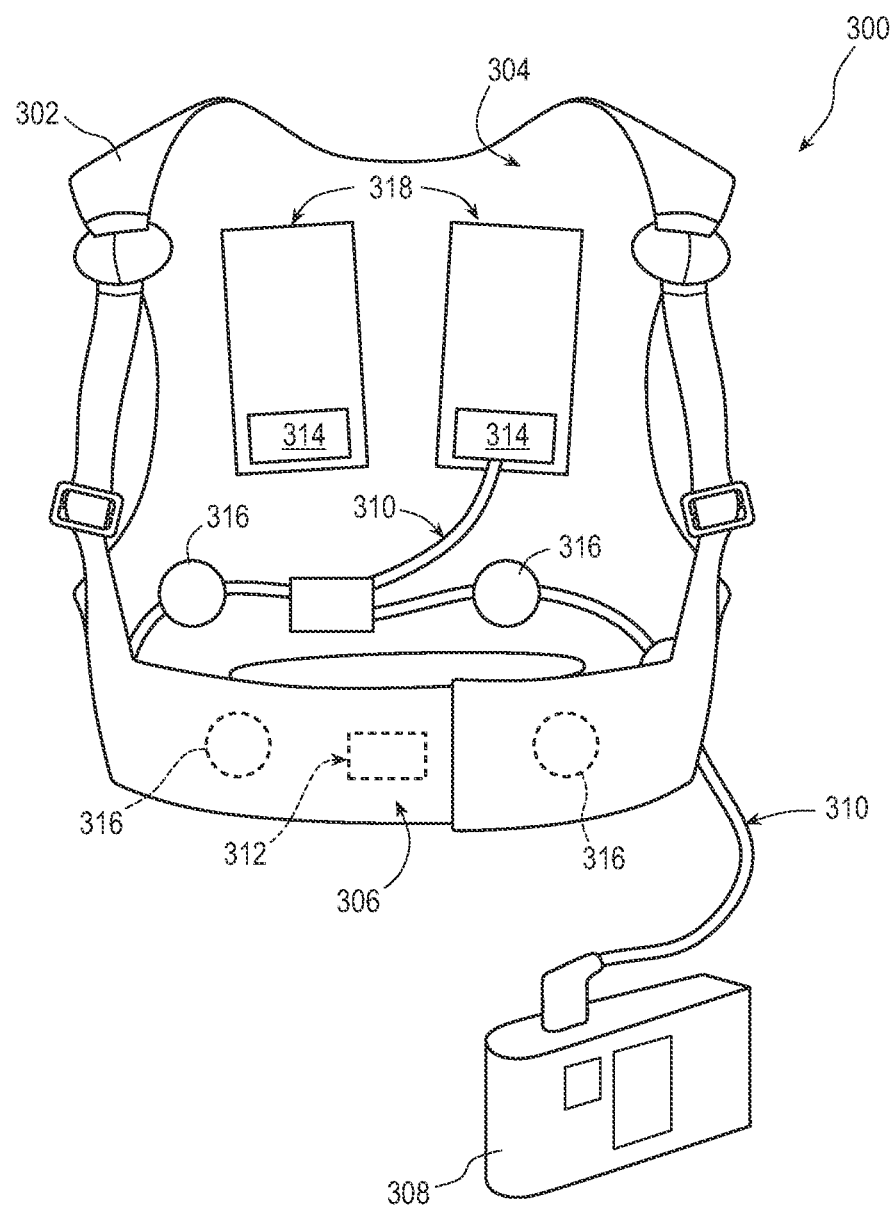
FIG. 3 is a diagram of sample embodiments of components of a WCD system in accordance with exemplary embodiments described herein.

FIG. 3 is a diagram of sample embodiments of components of a WCD system 300 according to exemplary embodiments. The WCD system 300 may be an example of the WCD system 104 described with reference to FIG. 1. In some embodiments, the WCD system 300 may include a support structure 302 comprising a vest-like wearable garment. In some embodiments, the support structure 302 has a backside 304 and a frontside 306 that closes in front of the chest of the patient.

In some embodiments, the WCD system 300 may also include an external defibrillator 308. The external defibrillator 308 may be an example of the defibrillator 108 described with reference to FIGS. 1 and 2. As illustrated, FIG. 3 does not show any support for the external defibrillator 308, but as discussed, the defibrillator 308 may be carried in a purse, on a belt, by a strap over the shoulder, and the like as discussed previously. One or more wires 310 may connect the external defibrillator 308 to one or more electrodes 312, 314, 316. Of the connected electrodes, electrodes 312, 314 are defibrillation electrodes, and electrodes 316 are ECG sensing electrodes.

The support structure 302 is worn by the patient to maintain electrodes 312, 314, 316 on a body of the patient. For example, the back-defibrillation electrodes 314 are maintained in pockets 318. In some embodiments, the inside of pockets 318 may comprise loose netting so that the electrodes 314 can contact the back of the patient. In some instances, a conductive fluid may be deployed to increase connectivity. Additionally, in some embodiments, sensing electrodes 316 are maintained in positions that surround the patient's torso for sensing ECG signals and/or the impedance of the patient.

In some instances, the ECG signals in a WCD system 300 may comprise too much electrical noise to be useful. To ameliorate the noise problem, multiple ECG sensing electrodes 316 are provided for presenting many options to the processor (e.g., processor 202, FIG. 2). The multiple ECG sensing electrodes 316 provide different vectors for sensing the ECG signal of the patient.

Figure 4:
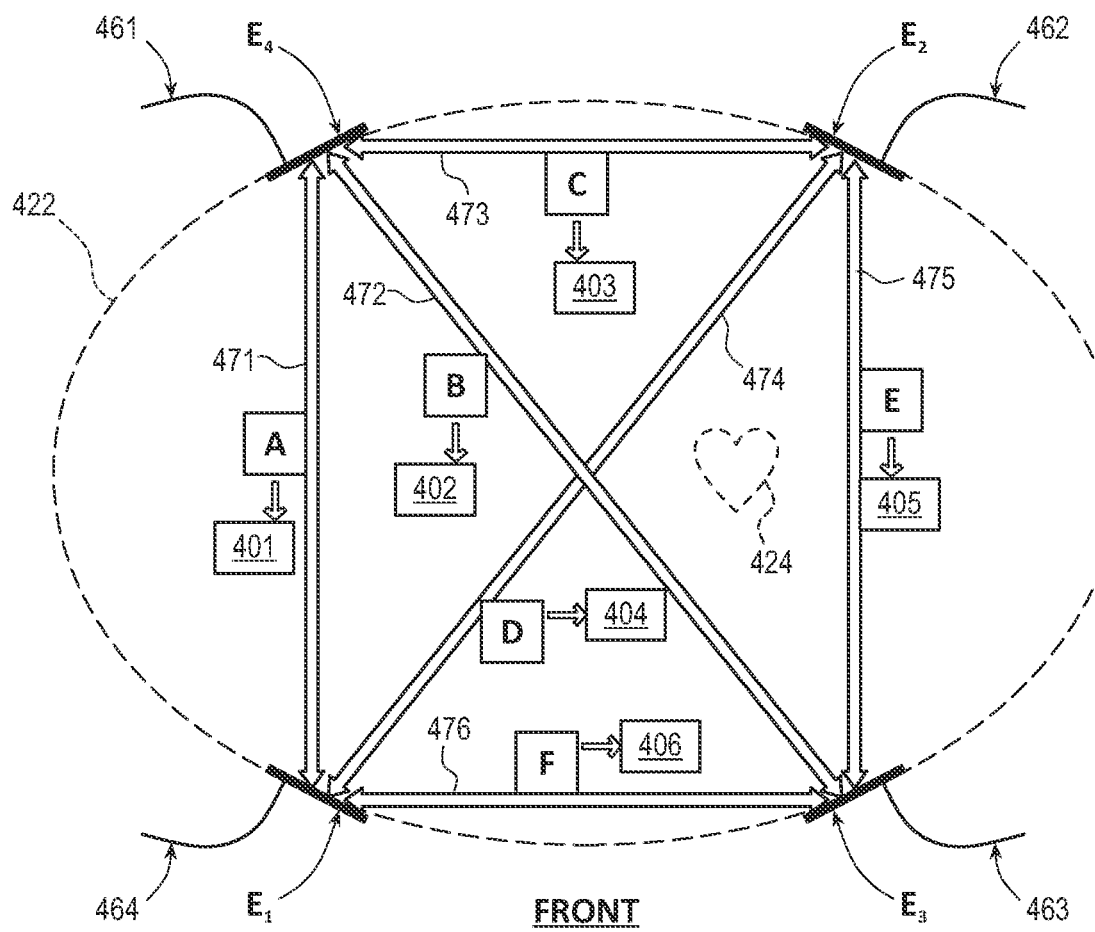
FIG. 4 is a conceptual diagram illustrating multiple electrodes of a WCD system in accordance with exemplary embodiments described herein.

FIG. 4 is a conceptual diagram illustrating how multiple electrodes of a WCD system may define a multi-vector embodiment for sensing ECG signals along different vectors according to various exemplary embodiments. A cross-section of a body of a patient 422 having a heart 424 is illustrated. In FIG. 4, the patient 422 is viewed from the top looking down, and the plane of FIG. 4 intersects patient 422 proximate the torso of the patient 422.

In some embodiments, four ECG sensing electrodes $E_1$, $E_2$, $E_3$, $E_4$ are maintained on the torso of patient 482 and have respective wire leads 461, 462, 463, 464. The electrodes $E_1$, $E_2$, $E_3$, $E_4$ that surround the torso may be similar to the sensing electrodes 316 as described with reference to FIG. 3.

Any pair of these four ECG sensing electrodes $E_1$, $E_2$, $E_3$, $E_4$ defines a vector along which an ECG signal may be sensed and, in some instances, measured. As such, electrodes $E_1$, $E_2$, $E_3$, $E_4$ define six vectors 471, 472, 473, 474, 475, 476.

These vectors 471, 472, 473, 474, 475, 476 define channels A, B, C, D, E, F, respectively. ECG signals 401, 402, 403, 404, 405, 406 may thus be sensed and/or measured from channels A, B, C, D, E, F, respectively, and in particular from the appropriate pairings of wire leads 461, 462, 463, 464 for each channel.

As shown in FIG. 4, electrodes $E_1$, $E_2$, $E_3$, $E_4$ are drawn on the same plane for simplicity, while in actuality, the electrodes $E_1$, $E_2$, $E_3$, $E_4$ may not be positioned on the same plane. Accordingly, vectors 471, 472, 473, 474, 475, 476 are not necessarily on the same plane, either. Further, in some embodiments, the WCD system averages a value of the voltages of all four electrodes electronically and then determines the voltage of each electrode relative to the average value. Conceptually, this average value is the signal at some point in space in between the electrodes $E_1$, $E_2$, $E_3$, $E_4$. It continuously changes its virtual position based on the voltages of the electrodes $E_1$, $E_2$, $E_3$, $E_4$. In some embodiments, this virtual point is referred to herein as the M Central Terminal (MCT). Relative to the MCT, there are four resulting vectors: E1C=E1−CM, E2C=E2−CM, E3C=E3−CM and E4C=E4−CM, where CM is the average voltage value. In some embodiments, the vectors are virtually formed by selecting a pair of these signals and subtracting one from the other. For example, E1C−E2C=(E1−CM)−(E2−CM)=E1−E2+(CM−CM)=E1−E2=E12. Although six vectors are described in FIG. 4, a different number of vectors may be used depending on the number of ECG electrodes present in the system and the desired number of vectors (up to the number of vectors that can be derived from the number of electrodes).

In some embodiments, to make the shock/no-shock determination as accurate as possible, a WCD system may assess the best ECG signals 401, 402, 403, 404, 405, 406 for rhythm analysis and interpretation. For example, ECG signals with the most noise may be ignored, discarded, or not considered, leaving the remaining ECG signals as candidates for the shock/no-shock determination.

In other embodiments, the vectors may be aggregated to make a shock/no-shock decision and/or to determine the patient's heart rate and/or QRS widths. For example, in some embodiments, the aggregation can be implemented as disclosed in U.S. Pat. No. 9,757,581 issued Sep. 12, 2017, entitled "Wearable Cardioverter Defibrillator Components Making Aggregate Shock/No Shock Determination from Two or More ECG Signals," which is incorporated herein by reference.

Figure 5:
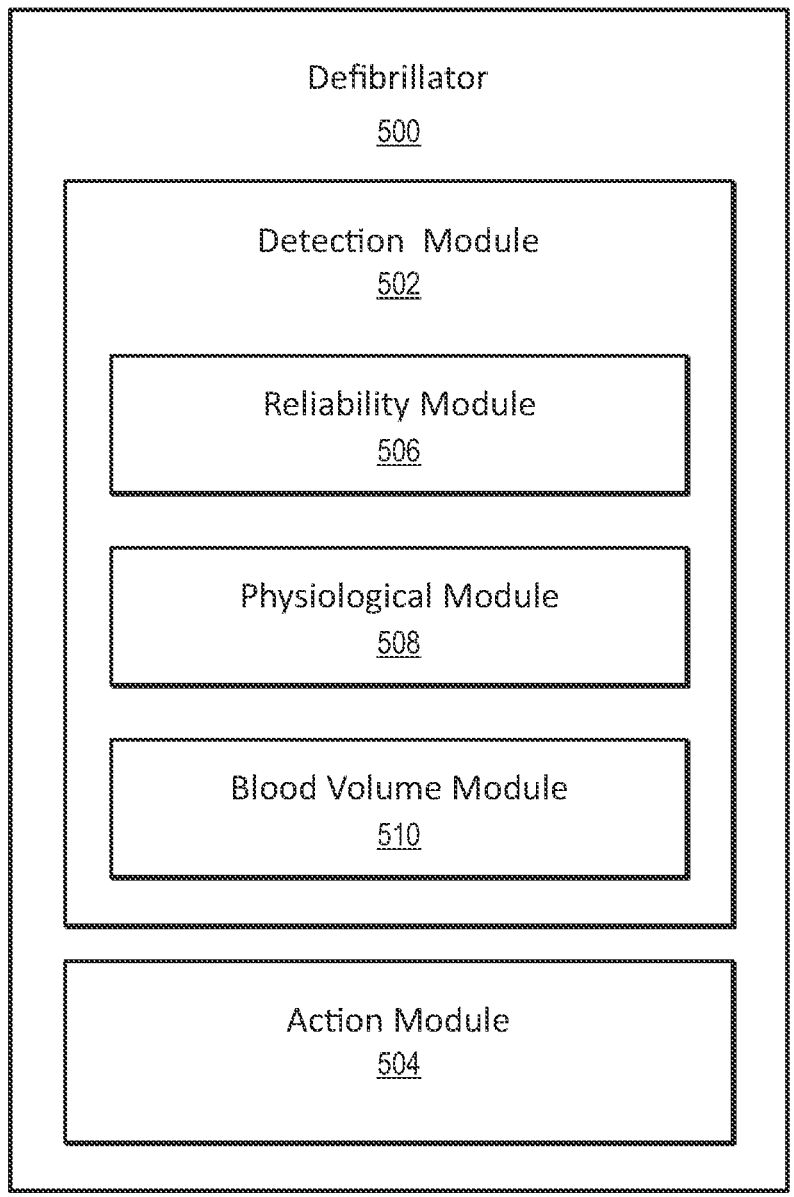
FIG. 5 is a is a block diagram of an example defibrillator in accordance with exemplary embodiments described herein.

FIG. 5 is a block diagram illustrating components of one example of a defibrillator 500. The defibrillator 500 may be an example of the defibrillator 108 described with reference to FIGS. 1 and 2 and defibrillator 308 described with reference to FIG. 3. In this example, the defibrillator 500 has detection module 502 and an action module 504. The detection module 502 may further include a reliability module 506, physiological module 508, and a blood volume module 510.

As described previously, because the WCD is worn by an ambulatory patient, patient movement may cause changes at the electrode-skin interface, resulting in noise on any or all of the ECG signals, which may interfere with ECG interpretation. The reliability module 506 may analyze the ECG signals to determine which signals are reliable and usable for a rhythm analysis.

When the patient wearing the WCD is moving, some ECG electrodes may move more than others, resulting in some ECG vectors having more noise than other ECG vectors. The reliability module 506 may assess the ECG vectors using a variety of methods to determine if ECG vectors have similar outputs across various analysis. If the assessments for an ECG vector have similar results, then the ECG vector is deemed reliable. The ECG vectors deemed to be reliable can then be used in a rhythm analysis, resulting in a more accurate result.

In some embodiments, the reliability module 506 may use multiple methods to analyze each ECG vector of the patient's heart rate. If the various methods used by the reliability module 506 result in a similar heartrate for a specific ECG vector, the reliability module 506 deems that specific ECG vector reliable. By using multiple different methods to analyze an ECG signal, the reliability module 506 has a heightened assurance of an accurate ECG signal when the results converge.

In some embodiments, the reliability module 506 may use two or more methods to determine if a cardiac event is occurring. In some embodiments, the reliability module 506 may be used multiple predetermined methods to assess the cardiac event or the ECG signal. In other embodiments, the reliability module 506 may be used a variety of methods with a variety of combinations to assess the signal.

Figure 6A:
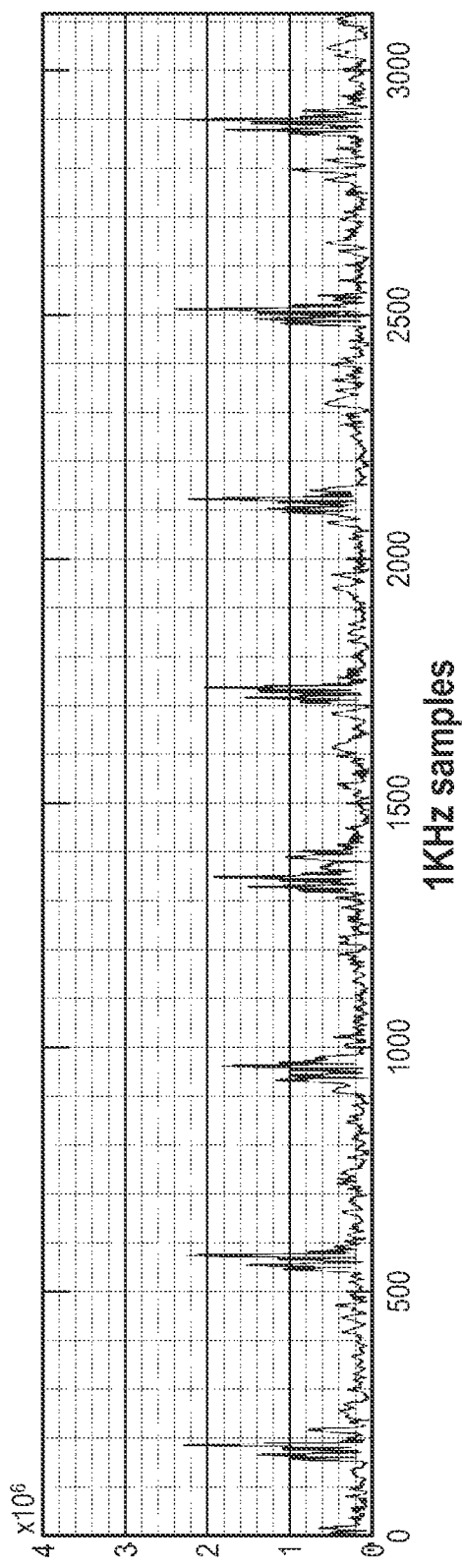
FIG. 6A illustrates an exemplary heart rate data graph for a predetermined time period in accordance with exemplary embodiments described herein.

For example, in some embodiments, the reliability module 506 may use both a frequency domain method and a time domain method to assess the ECG signal. In the example shown in FIG. 6A, the time domain method is a QRS detection method to determine the heartrate using the R-R interval between detected QRS complexes. FIG. 6A shows samples of a portion of a rectified ECG signal from a particular vector, sampled at a 1 KHz rate. There are about 391 samples on average between peaks, resulting in an average heart rate of about 153 bpm.

Figure 6B:
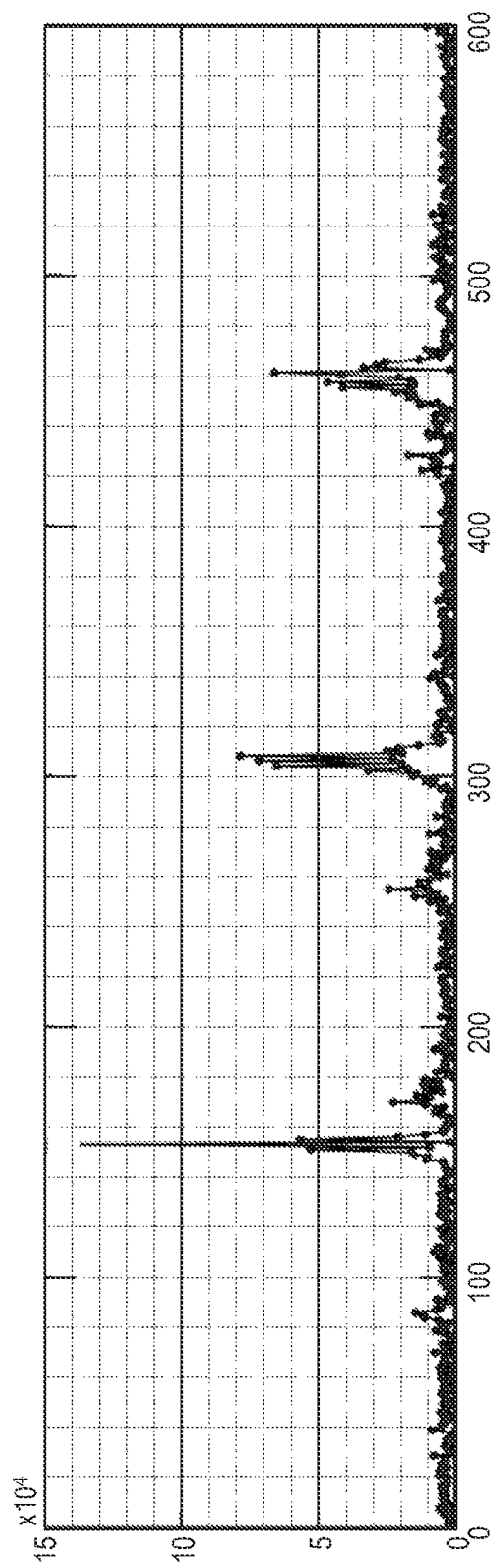
FIG. 6B illustrates an exemplary heart rate data graph for a predetermined time period in accordance with exemplary embodiments described herein.

In the example shown in FIG. 6B, the frequency domain method is an FTT method based on the same ECG portion of the same vector shown in FIG. 6A. As shown in FIGS. 6A and 6B, the harmonics of the heart rate are about 153 bpm apart, indicating the heartrate is relatively stable at about 153 bpm. For this ECG portion vector, the QRS assessment and the frequency domain assessment closely match, and the reliability module 506 indicates the ECG vector is reliable.

In some embodiments, the reliability module 506 may use various criteria to determine whether different assessments match. The criteria may include: the difference between the values is within a predetermined range (e.g., ±5 bpm for the example shown in FIGS. 6A and 6B), the percentage difference is within a predetermined threshold (e.g., 3.5%), and the like. In other embodiments, the reliability module 506 may use different criteria for determining matching ECG vectors.

Figure 7A:
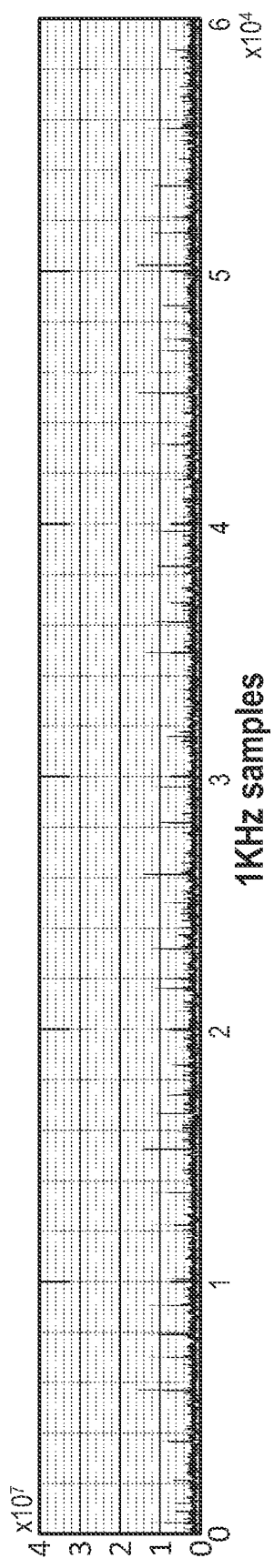
FIG. 7A illustrates an exemplary heart rate data graph for a predetermined time period in accordance with exemplary embodiments described herein.
Figure 7B:
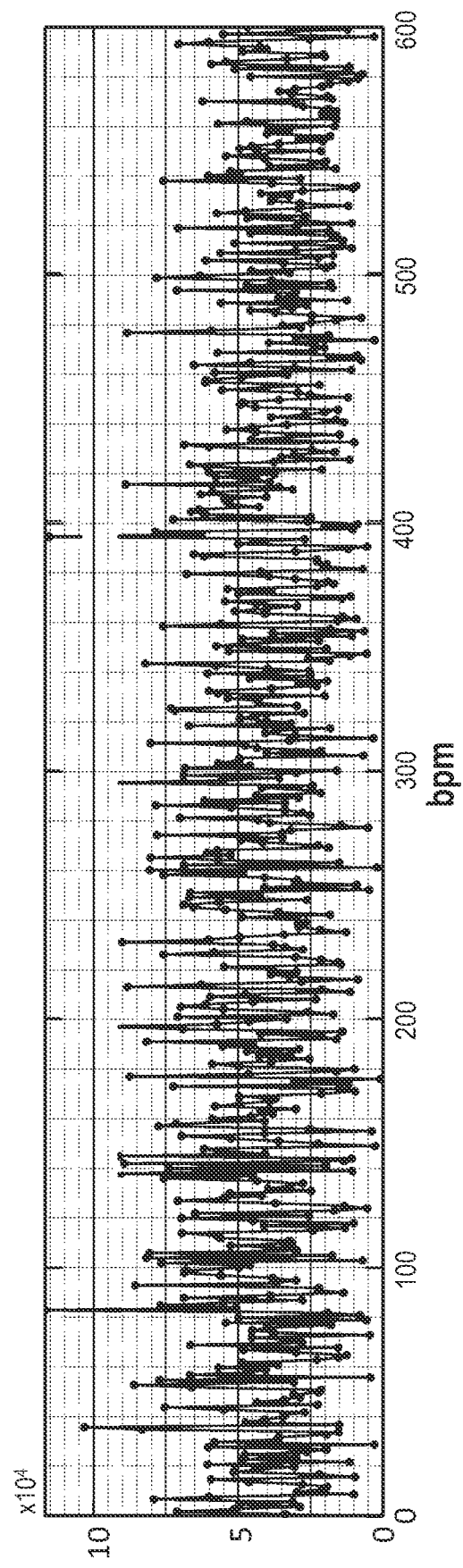
FIG. 7B illustrates an exemplary heart rate data graph for a predetermined time period in accordance with exemplary embodiments described herein.

Another example of the reliability module 506 assessment is shown in FIGS. 7A and 7B. FIG. 7A shows a rectified ECG signal and FIG. 7B shows an FFT portion of an ECG signal from a separate vector. The time domain assessment based on the QRS detection results in a heartrate of about 103 bpm, whereas the frequency domain assessment based on the FFT results shows a heartrate of about 197 bpm. The reliability module 506 will determine the heart rates do not match and indicate to the detection module 502 that the ECG vector is unreliable.

Referring back to FIG. 5, the reliability module 506 may use varies criteria in assessing the vectors. For example, the criteria may include defining ranges for the assessment that include: a criteria for matching (i.e., a reliable vector), criteria for unmatching (i.e., unreliable vector) with the range between the two criteria being indeterminate. For example, the criteria for a reliable vector may be preset as the difference between the HRs being within 5-15 beats per minute. In some embodiments, it may be within 10 beats per minute. In some embodiments, the criteria for an unreliable vector may be preset as the heart rates having a percentage difference greater than 10%. Differences in HRs between these two criteria would be indeterminate, which can be addressed by setting a default HR determining method and deciding the HR for that vector being the HR from the default HR determining method; tracking the history of that vector for being deemed reliable/unreliable and if the recent history shows the vector is unreliable for previous portions of ECG, deeming this vector unreliable for this particular portion of ECG. In other embodiments, different criteria for determining how to handle indeterminate vectors can be used.

Although in the examples above, the reliability module 506 uses time domain and frequency domain assessments described above, in other embodiments, the reliability module 506 may use different assessments. For example, methods of detecting R-R interval can include those that do not rectify the ECG signal. Other assessments can include without limitation, adaptive signal processing (including Kalman filtering), independent component analysis, principal component analysis. Further enhancements can include using adaptive learning techniques to accommodate changes in physiological signals that can vary over time.

As stated above, if the system uses only a single vector or channel, then the portions of ECG that are unreliable can be omitted from the rhythm analysis. For systems with multiple vectors or channels, if the reliability module 506 finds multiple channels that meet the selection criteria, the rhythm analysis is determined with a mathematical combination of the results of the reliable channels. For example, the mathematical combination could be the median value of the measurements (e.g., HR) of the reliable channels, or a mean of the measurements of the reliable channels. In some embodiments, the reliability module 506 may estimate a consistency for each channel and used the consistency to calculate a weighted average. The weighted average could include all available channels, or exclude channels that are deemed unreliable and indeterminate, only the channels deemed reliable, or the N most closely matched channels (e.g., where N might be 3 in a system having 4 or more channels). In some embodiments, if the reliability module 506 finds only one channel reliable in a multi-channel system, then the analysis would be reduced to just that channel. In some embodiments, if no channel is reliable, then the rhythm analysis may be omitted.

In some embodiments, the physiological module 508 may assess various physiological parameters to assist in a shockable event determination. The physiological module 508 may assess physiological parameters such as heartrate, blood pressure, respiratory rate, blood glucose level, sleep state, and the like. For example, heart rate can also be estimated from electroencephalography (EEG) signals, and sleep state can be estimated using brain wave signals or EEG signals. However, such physiological signals can be severely corrupted by external noise, artifact, and/or signals from other unwanted signal sources (e.g., the mother's QRS complexes when trying to detect fetal QRS complexes). The noise can be more severe when a physiological signal is collected with small, wearable, portable and non-invasive monitors.

In some embodiments, the detection module 502 may include a blood volume module 510. The blood volume module 510 may receive data from a sensor capable of sensing a volume of blood in a portion of the patient's body. In one embodiment, the detection module 502 may couple to a device which may track blood volume, heart rate, temperature, and activity or accelerometer signals. The blood volume module 510 may communicate with the reliability module 506 to ensure the reliability of ECG signals. For example, the blood sensor may have less noise artifact in normal conditions than electrodes and can be used determining whether to deem a channel as unreliable if the heart rate from that channel is significantly different from that provided by the blood sensor.

Further, in some embodiments, the blood volume module 510 may use blood volume measurements from the blood volume sensor to improve the accuracy of shock/no shock decisions made by the detection module 502. For example, when the rhythm analysis indicates a shock decision, but the blood volume data from the blood volume sensor indicates a stable blood volume, the action module 504 may delay or abort the shock as unnecessary. A stable blood volume may mean a blood volume measurement that indicates the patient is perfusing in a regular manner.

In some embodiments, the blood volume module 510 may also indicate a shockable condition when the detection module 502 has not found a shockable condition. If the rhythm analysis indicates a no shock decision but the blood volume module 510 indicates an unstable blood volume, the action module 504 may start the shock delivery process. In some embodiments, the blood volume module 510 may only indicate a shockable condition in a monitor zone. A monitor zone may include a non-shockable VT in which the patient's ECG is continuously monitored rather than a normal periodic monitoring. In some embodiments, a monitor zone may be set to a range of heart rate below the VT rate threshold. For example, if the VT rate threshold is 170 bpm, the monitor zone may be set to a range between 150 bpm and 170 bpm. However, if the blood volume module 510 indicates that the blood volume is stable or indeterminate, the detection module 502 will continue to continuously monitor the patient.

In some embodiments, the blood volume module 510 may receive and store the blood volume to sense and store a baseline blood volume metric as part of a set-up procedure. Once the set-up procedure is complete, the blood volume module 510 may have the blood sensor enter a low power mode. The blood volume module 510 may then activate the blood volume sensor to measure blood volume in response to the detection module 502 detecting an elevated heart rate. The blood volume module 510 may then compare the new blood volume measurements to the stored baseline and determine whether the blood is stable/unstable. If the blood volume is unstable, the action module 504 may take one or more actions, including issue an alert or beginning a shock sequence. By allowing the blood volume sensor to enter a sleep mode, the blood volume module 510 may prolong the time the blood volume sensor can operate without being recharged.

The action module 504 may use channels identified by the reliability module 506 to make a shock/no-shock decision.

The action module 504 may analyze the heart rate and QRS data from the consistent channels to determine if the patient is having a cardiac event. In further embodiments, the action module 504 may also use parameters form the physiological module 508 and the blood volume module 510 to make a shock/no-shock decision.

At the same time, in some embodiments, the action module 504 may alert the patient of a potential electrode connectivity issue based at least in part on the inconsistent channels. For example, the consistency module 506 may ascertain common electrodes in inconsistent channels and pass this information on to the action module 504. The action module 504 may then cause an alert to be issued to the patient to troubleshoot the issue.

In some embodiments, the action module 504 may prompt the patient to reduce activity if the number of ECG portions the reliability module 506 finds unsuitable exceeds a threshold. This can reduce the amount of noise generated by the patient's movement and increase the number of ECG portions that are deemed reliable.

The action module 504 may also use a combination of heart rate and QRS widths to make shock/no-shock decisions. The action module 504 may use methods similar to those disclosed in U.S. Pat. No. 10,016,614 entitled "Wearable Cardioverter Defibrillator (WCD) System Making Shock/No Shock Determinations by Aggregating Aspects of Multiple Patient Parameters" or U.S. Pat. No. 10,105,547 entitled "Wearable Cardioverter Defibrillator (WCD) Causing Patient's WRS Width to be Plotted Against the Heart Rate," both of which are incorporated by reference herein.

Figure 8:
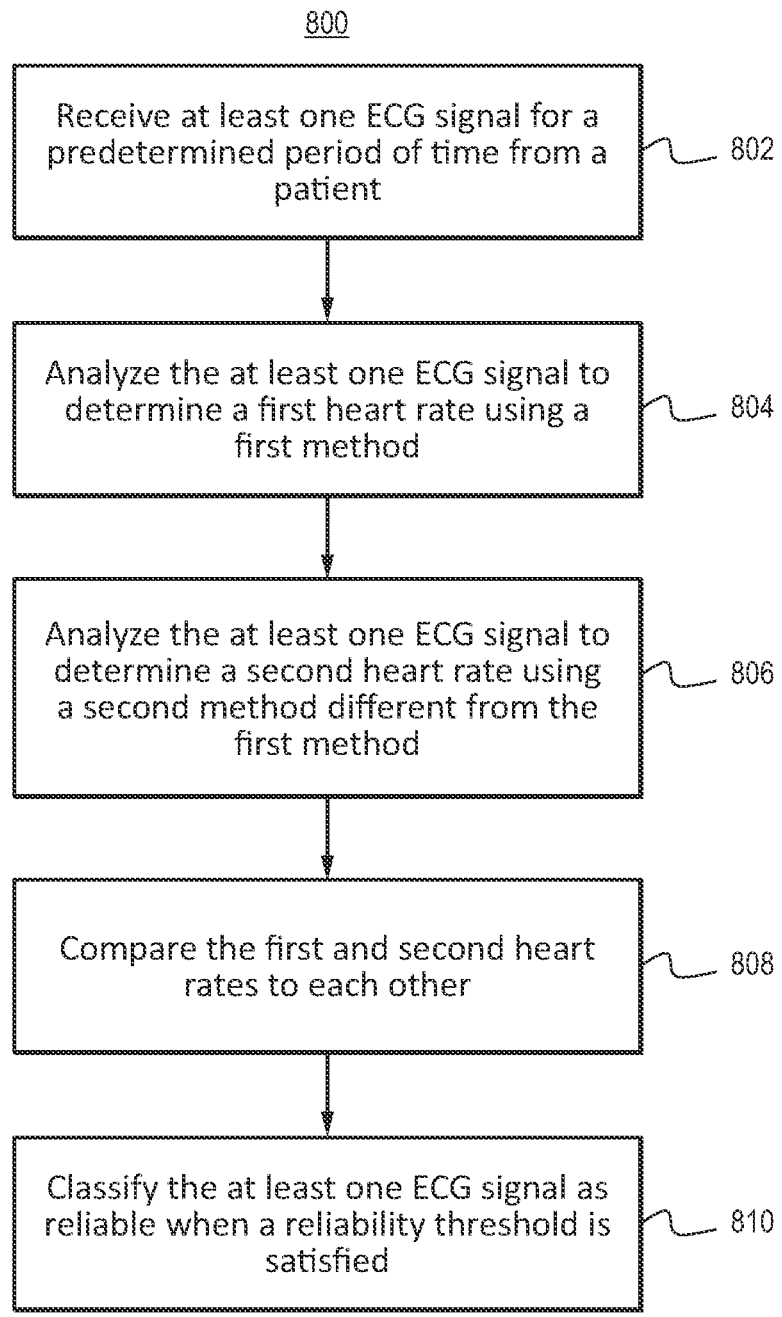
FIG. 8 is an exemplary flow diagram in accordance with exemplary embodiments described herein.

FIG. 8 is a flow chart illustrating an example of a method 800 for WCD systems, in accordance with various aspects of the present disclosure. For clarity, the method 800 is described below with reference to aspects of one or more of the systems described herein.

At block 802, the method 800 may receive at least one ECG signal for a predetermined period of time from a patient. The patient may be wearing a WCD system. The patient may have at least three ECG sensing electrodes attached to their skin and obtaining a signal. In some embodiments, the method 800 may receive multiple ECG signals. The predetermined period of time may be a snapshot in time or a continuously moving period of time.

In some embodiments, a patient may have sensing electrodes coupled to or somehow attached to them in such a way that the electrodes may sense a heart signal from the patient. The method 800 may obtain a signal from each of the at least three sensing electrodes. The method 800 may also define at least three channels between the at least three electrodes and obtain heart data for a predetermined time period from the at least three channels. The predetermined time period may be a snapshot of an ambulatory period for the patient. In some embodiments, the predetermined time period may be between five (5) seconds and two (2) minutes.

At block 804, the method 800 may analyze the at least one ECG signal to determine a first heart rate using a first method. At block 806, the method may analyze the at least one ECG signal to determine a second heart rate using a second method different from the first method. In some embodiments, the first method may be a time domain method and the second method may be a frequency domain method. In some embodiments, the first or second method may include adaptive signal processing, Kalman filtering, independent component analysis, and principal component analysis.

At block 808, the method 800 may compare the first and second heart rates to each other. At block 810, the method may classify the at least one ECG signal as reliable when a reliability threshold is satisfied. In some embodiments, the at least one ECG signal is classified as reliable when the first and second heart rates are within a predetermined number of beats. In some embodiments, the predetermined number of beats is within five to fifteen beats per minute. In some embodiments, the predetermined number of beats is within ten beats per minute. In further embodiments, the at least one ECG signal is classified as reliable when the first and second heart rates are within a predetermined percentage difference. In some embodiments, the predetermined percentage difference is less than twenty percent. In some embodiments, the predetermined percentage is approximately 10 percent.

In some embodiments, the method 800 may classify the at least one ECG signal as unreliable when an unreliability threshold is satisfied. The unreliability threshold may be equal to or greater than seven percent.

In some embodiments, the method 800 may perform a rhythm analysis using at least the first heart rate when the ECG signal is classified as reliable. In some embodiments, the method 800 may use an average of both the first and second heart rate or a median of the two heart rates. In further embodiments, if more than one channel is deemed reliable, the method 800 may perform a rhythm analysis using a mathematical combination of heart rates from the at least two ECG signals. For example, the method 800 may use an average, median, or other value derived from the multiple reliable heart rate calculations.

Thus, the method 800 may provide for determining reliable ECG channels. It should be noted that the method 800 is just one implementation and that the operations of the method 800 may be rearranged or otherwise modified such that other implementations are possible.

Figure 9:
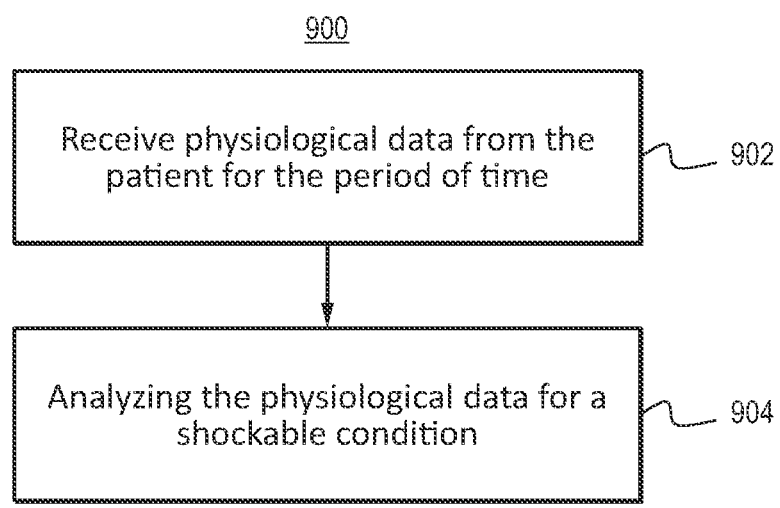
FIG. 9 is another exemplary flow diagram in accordance with exemplary embodiments described herein.

FIG. 9 is a flow chart illustrating an example of a method 900 for WCD systems, in accordance with various aspects of the present disclosure. For clarity, the method 900 is described below with reference to aspects of one or more of the systems described herein.

At block 902, the method 900 may receive physiological data from the patient for the period of time. The physiological data may include heartrate, blood pressure, respiratory rate, blood glucose level, activity level, sleep state, and the like. For example, heart rate variability can also be estimated from electroencephalography (EEG) signals, and sleep state can be estimated using brain wave signals or EEG signals. Respiratory rate and activity level such as accelerometer data can indicate a patient is working out or moving.

At block 904, the method 900 may analyze the physiological data for a shockable condition. In some embodiments, the method 900 may compare the physiological data to heart rate data. For example, the physiological data may support or contrast a shockable condition.

Thus, the method 900 may provide for determining reliable ECG signals. It should be noted that the method 900 is just one implementation and that the operations of the method 900 may be rearranged or otherwise modified such that other implementations are possible.

A person skilled in the art will be able to practice the present invention after careful review of this description, which is to be taken as a whole. Details have been included to provide a thorough understanding. In other instances, well-known aspects have not been described in order to not unnecessarily obscure this description.

Some technologies or techniques described in this document may be known. Even then, however, it is not known to apply such technologies or techniques as described in this document or for the purposes described in this document.

This description includes one or more examples, but this fact does not limit how the invention may be practiced. Indeed, examples, instances, versions, or embodiments of the invention may be practiced according to what is described, or yet differently, and also in conjunction with other present or future technologies. Other such embodiments include combinations and sub-combinations of features described herein, including, for example, embodiments that are equivalent to the following: providing or applying a feature in a different order than in a described embodiment; extracting an individual feature from one embodiment and inserting such feature into another embodiment; removing one or more features from an embodiment, or both removing a feature from an embodiment and adding a feature extracted from another embodiment while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to," "adapted to," and/or "configured to" denote one or more actual states of construction, adaptation, and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

Reference numerals: In this description, a single reference numeral may be used consistently to denote a single item, aspect, component, or process. Moreover, a further effort may have been made in the preparation of this description to use similar though not identical reference numerals to denote other versions or embodiments of an item, aspect, component, or process that are identical or at least similar or related. Where made, such a further effort was not required but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component, or process rather than its reference numeral. Any similarity in reference numerals may be used to infer a similarity in the text, but not to confuse aspects where the text or other context indicates otherwise.

The claims of this document define certain combinations and subcombinations of elements, features, and acts or operations, which are regarded as novel and non-obvious. The claims also include elements, features, and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A method for monitoring a heart of a patient performed by a wearable cardioverter defibrillator (WCD) system that comprises a WCD, the method comprising:
   receiving, from one or more electrocardiogram (ECG) sensors, at least one ECG signal for a period of time from the patient;
   analyzing the at least one ECG signal to determine a first heart rate using a first method;
   analyzing the at least one ECG signal to determine a second heart rate using a second method different from the first method;
   comparing the first and second heart rates to each other;
   determining a difference between the first and second heart rates;
   determining from the difference whether a reliability threshold is satisfied;
   classifying the at least one ECG signal as reliable responsive to determining that the reliability threshold is satisfied; and
   providing defibrillation therapy to the patient based, at least in part, on the at least one ECG signal being classified as reliable.

2. The method of claim 1, wherein providing defibrillation therapy further comprises performing a rhythm analysis using at least the first heart rate when the at least one ECG signal is classified as reliable.

3. The method of claim 2, wherein the at least one ECG signal comprises at least two ECG signals, and further comprising:
   performing the rhythm analysis using a combination of heart rates of the at least two ECG signals.

4. The method of claim 3, wherein the at least two ECG signals are classified as reliable based on the combination, wherein the combination comprises a weighted average of the at least two ECG signals.

5. The method of claim 1, wherein the first method is a time domain method and the second method is a frequency domain method.

6. The method of claim 1, wherein determining from the difference whether the reliability threshold is satisfied comprises determining whether the first and second heart rates are within a predetermined number of beats per minute.

7. The method of claim 6, wherein the predetermined number of beats per minute being five to fifteen beats per minute.

8. The method of claim 1, wherein determining from the difference whether the reliability threshold is satisfied comprises determining whether the first and second heart rates are within a predetermined percentage difference.

9. The method of claim 8, wherein the predetermined percentage difference is less than twenty percent.

10. The method of claim 9, wherein the predetermined percentage difference is ten percent.

11. The method of claim 1, further comprising:
determining from the difference whether an unreliability threshold is satisfied; and
classifying the at least one ECG signal as unreliable responsive to determining that the unreliability threshold is satisfied.

12. The method of claim 11, wherein the unreliability threshold is equal to or greater than ten percent.

13. The method of claim 1, wherein the first method includes one of an adaptive signal processing, Kalman filtering, independent component analysis, or principal component analysis.

14. The method of claim 1, wherein receiving at least one ECG signal comprises receiving three or more channels.

15. The method of claim 1, wherein the at least one ECG signal includes two channels and the at least one ECG signal being classified as reliable when the two channels are classified as reliable.

16. The method of claim 1, further comprising:
receiving physiological data from the patient for the period of time; and
analyzing the physiological data to determine if a shockable condition is indicated.

17. The method of claim 16, wherein the physiological data includes blood volume data.

18. The method of claim 17 further comprising:
determining whether a shockable condition is present based, at least in part, on the blood volume data.

19. A method for monitoring a heart of a patient performed by a wearable cardioverter defibrillator (WCD) system that comprises a WCD, the method comprising:
receiving, from one or more electrocardiogram (ECG) sensor, at least one ECG signal for a period of time from the patient;
analyzing the at least one ECG signal to determine a first heart rate using a first method;
analyzing the at least one ECG signal to determine a second heart rate using a second method different from the first method, the first method being a time domain method and the second method being a frequency domain method;
comparing the first and second heart rates to each other;
determining a difference between the first and second heart rates;
determining from the difference whether a reliability threshold is satisfied;
classifying the at least one ECG signal as reliable responsive to determining that the reliability threshold is satisfied;
performing a rhythm analysis using at least the first heart rate when the at least one ECG signal is classified as reliable; and
providing defibrillation therapy to the patient based, at least in part, on the at least one ECG signal being classified as reliable.

20. The method of claim 19 further comprising:
determining from the difference whether an unreliability threshold is satisfied; and
classifying the at least one ECG signal as unreliable responsive to determining that the unreliability threshold is satisfied.

* * * * *